United States Patent
Schwartzmiller et al.

(10) Patent No.: US 6,200,596 B1
(45) Date of Patent: Mar. 13, 2001

(54) SKIN TREATMENT WITH ADHESION ENHANCEMENT PROPERTIES

(75) Inventors: Donald H. Schwartzmiller, Oakdale; Neil A. Randen, Stillwater, both of MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 08/186,226

(22) Filed: Jan. 21, 1994

Related U.S. Application Data

(63) Continuation of application No. 07/951,236, filed on Sep. 25, 1992, now abandoned.

(51) Int. Cl.[7] .............................. A61F 13/00; A61K 7/48
(52) U.S. Cl. .................... 424/448; 424/78.02; 424/78.06
(58) Field of Search .................. 424/401, 78.02, 424/448

(56) References Cited

U.S. PATENT DOCUMENTS

| | | | |
|---|---|---|---|
| 2,804,073 | * 8/1957 | Gallienne et al. ............... | 424/78.02 |
| 3,911,105 | 10/1975 | Papantoniou . | |
| 3,987,000 | * 10/1976 | Gleichenhagen et al. .......... | 526/325 |
| 4,057,622 | 11/1977 | Hase et al. . | |
| 4,057,623 | 11/1977 | Hase et al. . | |
| 4,057,624 | 11/1977 | Hase et al. . | |
| 4,128,634 | 12/1978 | Hase et al. . | |
| 4,128,635 | 12/1978 | Hase et al. . | |
| 4,128,636 | 12/1978 | Hase et al. . | |
| 4,172,122 | 10/1979 | Kubik et al. . | |
| 4,552,755 | 11/1985 | Randen . | |
| 4,816,256 | 3/1989 | Randen . | |
| 4,867,981 | * 9/1989 | Grof ...................................... | 424/448 |
| 4,931,282 | * 6/1990 | Asmus et al. ......................... | 424/448 |
| 4,940,579 | 7/1990 | Randen . | |
| 5,132,115 | * 7/1992 | Wolter et al. ......................... | 424/448 |
| 5,133,970 | * 7/1992 | Petereit et al. ....................... | 424/448 |
| 5,151,271 | * 9/1992 | Otsuka et al. ........................ | 424/448 |

FOREIGN PATENT DOCUMENTS

| | | |
|---|---|---|
| 603376 | 4/1988 | (AU) . |
| 0 265 087 | 4/1988 | (EP) . |
| 0 265 228 | 4/1988 | (EP) . |
| 0 268 164 | 5/1988 | (EP) . |
| 0 376 533 | 7/1990 | (EP) . |
| 0 429 156 A1 | 5/1991 | (EP) . |
| 2 232 302 | 1/1975 | (FR) . |
| 2 398 496 | 2/1979 | (FR) . |
| 4538707 | * 12/1970 | (JP) .................................. 424/78.02 |
| 54-151139 | 11/1979 | (JP) . |
| 55-130907 | 10/1980 | (JP) . |
| Wo 91/16037 | 10/1991 | (WO) . |

OTHER PUBLICATIONS

*Polymer Handbook* (edited by Bandrup and Immergut) pp. IV–344–358 (1966).

* cited by examiner

*Primary Examiner*—Peter F. Kulkosky
(74) *Attorney, Agent, or Firm*—Stephen W. Bauer; Carolyn A. Bates; Jennie G. Boeder

(57) ABSTRACT

Skin treatments which do not interfere with the ability of pressure-sensitive adhesives to adhere to skin are disclosed. The treatment compositions include an acrylate polymer dissolved in an emollient oil. Use of the treatment provides a method of protecting mammalian skin without interfering with the application of medical adhesive dressings.

17 Claims, No Drawings

SKIN TREATMENT WITH ADHESION ENHANCEMENT PROPERTIES

This is a continuation of application Ser. No. 07/951,236 filed Sep. 25, 1992, now abandoned.

TECHNICAL FIELD

This invention relates to a method which enhances the ability of pressure sensitive adhesives to adhere to treated mammalian skin. More particularly, the invention relates to moisturizing skin treatments that medical adhesives will adhere to.

BACKGROUND ART

Most of the moisturizing lotions and ointments commonly used to treat and protect mammalian skin consist of oil-in-water emulsions and creams, water-in-oil emulsions and, to a lesser degree, simply 100% oil formulations. These compositions generally use oils as the main ingredient with lesser amounts of humectants. The oils are selected from a large group of commercially available, cosmetically accepted oils, which are generally recognized by the cosmetic industry as having emollient properties. As a whole, these products either do not allow or do not enhance the ability of adhesive products, such as medical tapes, to adhere over skin to which they have been applied.

According to the present invention, it has been discovered that certain oil-soluble acrylate polymers, alone or in combination with conventional moisturizing oils, in oil-in-water or water-in-oil emulsions, provide substantive (i.e., they are not readily removed by simple abrasion or water assault) skin treatments which enhance the ability of pressure sensitive adhesives to adhere to the treated skin.

Oil-soluble acrylate polymers have been used heretofore in treatments for skin. For example, acrylate polymers have been used in sunscreening compositions of the oil or water-in-oil type to reduce removal of the sunscreening agent from the skin by swimming or perspiration (U.S. Pat. No. 4,172,122); in skin moisturizing compositions (U.S. Pat. No. 4,552,755); with medicaments for topical application to the skin (U.S. Pat. No. 4,940,579); and in mosquito repellent compositions (U.S. Pat. No. 4,816,256).

Other cosmetic compositions containing oil-soluble acrylate polymers include make-up compositions such as lip rouges, mascaras and eyeliners (U.S. Pat. No. 3,911,105; Japanese Patent Application Publication No. 54-151139; and Japanese Patent Application Publication No. 55-130907).

Water-in-oil emulsion composition for skin treatment containing low molecular weight oil-soluble acrylate copolymers as emulsifying agents are disclosed in U.S. Pat. Nos. 4,057,622; 4,057,623; 4,057,624; 4,128,634; 4,128,635; 4,128,636. However, prior to the present invention, it had not been recognized that certain oil-soluble acrylate polymers can provide skin treatment compositions which enhance the ability of pressure sensitive adhesives to adhere to skin. When these oil-soluble acrylate polymers are used with emollient oils in oil-in-water or water-in-oil emulsions, the result is a skin treatment which provides not only long lasting skin moisturizing effects but the unexpected property that pressure sensitive adhesives will adhere to them.

SUMMARY OF THE INVENTION

According to the present invention, there is provided a method of increasing, or at least not adversely affecting, the adhesion of pressure sensitive adhesives to treated mammalian skin. The method comprises coating the skin with the coating composition prior to the application of the pressure sensitive adhesive. The coating composition comprises an acrylate polymer dissolved in an emollient oil. The acrylate polymer comprises:

from 40 to 95 mole percent of the same or different ester monomers of the formula:

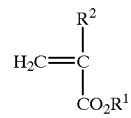

wherein $R^1$ is an alkyl radical containing 4 to 18 carbon atoms in cyclic, straight- or branched-chain configuration, and $R^2$ is hydrogen or lower alkyl containing 1 to 4 carbon atoms; and from 5 to 60 mole percent by weight of the same or different acid monomers of the formula:

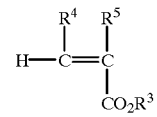

wherein $R^3$ is H or an alkyl group containing 1 to 18 carbon atoms;

$R^4$ is hydrogen, methyl, or —$CO_2R^3$, and $R^5$ is hydrogen, lower alkyl or —$CH_2CO_2R^3$;

provided when $R^4$ is not hydrogen, $R^5$ is hydrogen and when $R^5$ is not hydrogen, $R^4$ is hydrogen, and further provided that at least one $R^3$ is hydrogen.

The acrylate polymer when used in oil-in-water and water-in-oil emulsions provide moisturizing, substantive, adhesion enhancing treatments for mammalian skin.

DETAILED DESCRIPTION OF THE INVENTION

Acrylate polymers useful in the practice of the invention include copolymers, terpolymers, etc. derived from the polymerization of at least one ester monomer and at least one acid monomer. The ester monomer is selected from the same or different monomers of Formula I below:

Formula I

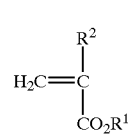

wherein $R^1$ is an alkyl radical containing 4 to 18 carbon atoms in cyclic, straight- or branched-chain configuration, and $R^2$ is hydrogen or lower alkyl.

The acid monomer is selected from the same or different monomers of Formula II below:

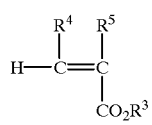

Formula II wherein
R³ is H or an alkyl group containing 1 to 18 carbon atoms;
R⁴ is hydrogen, methyl, or —CO₂R³, and
R⁵ is hydrogen, lower alkyl or —CH₂CO₂R³;
provided when R⁴ is not hydrogen, R⁵ is hydrogen and when R⁵ is not hydrogen, R⁴ is hydrogen, and further provided that at least one R³ is hydrogen. The term "lower alkyl" refers to an alkyl radical containing one to four carbon atoms.

The acrylate polymers can be prepared using the corresponding alkyl esters of acrylic, methacrylic, itaconic or malic acid, wherein the ester alkyl groups may contain 1 to 18 carbon atoms and are exemplified by methyl, ethyl, butyl, methylisoamyl, n-hexyl, 2-ethylhexyl, isooctyl, isodecyl, lauryl, octadecyl, stearyl groups and the like. The most preferred esters are the acrylates and methacrylates with alkyl groups containing 6 to 18 carbon atoms. Esters wherein the alkyl group contains less than four carbon atoms may be included in small amounts, e.g. less than 10 mole percent. However, in order to achieve the requisite solubility parameter, the polymers should generally not contain a significant amount of lower alkyl ester monomers. The preferred ester monomers of Formula I include alkyl esters such as:

n-butyl acrylate
n-butyl methacrylate
iso-butyl acrylate
iso-butyl methacrylate
sec-butyl acrylate
sec-butyl methacrylate
n-amyl acrylate
n-amyl methacrylate
iso-amyl acrylate
iso-amyl methacrylate
n-hexyl acrylate
n-hexyl methacrylate
cyclohexyl acrylate
2-ethylbutyl acrylate
2-ethylbutyl methacrylate
n-heptyl acrylate
n-heptyl methacrylate
n-octyl acrylate
n-octyl methacrylate
2-ethylhexyl acrylate
2-ethylhexyl methacrylate
iso-octyl acrylate
iso-octyl methacrylate
n-nonyl acrylate
n-nonyl methacrylate
n-decyl acrylate
n-decyl methacrylate
iso-decyl acrylate
iso-decyl methacrylate
undecyl methacrylate
lauryl acrylate
lauryl methacrylate
hexadecyl acrylate
hexadecyl methacrylate
octadecyl acrylate
octadecyl methacrylate
stearyl methacrylate
β-carboxyethyl acrylate, and mixtures thereof.

The preferred acid monomers are the unesterified α,β-olefinically unsaturated carboxylic acids of Formula II such as acrylic acid, methacrylic acid, maleic acid, itaconic acid, ethacrylic acid and mixtures thereof. The presence of the carboxylic acid monomer contributes to the substantivity of the compositions and the ability of adhesives to adhere to skin coated with these compositions.

The acrylate polymers are derived from about 5 to 60 mole percent of the acid monomers and about 40 to 95 mole percent of the alkyl ester monomers. The preferred polymers are derived from 10 to 40 mole percent of the olefinically unsaturated carboxylic acid monomers and 90 to 60 mole percent of the alkyl ester monomers containing 4 to 18 carbon atoms in the ester alkyl groups. The most preferred polymers are derived from 15 to 30 mole percent of the olefinically unsaturated carboxylic acid monomers and 70 to 85 mole percent of the alkyl ester monomers containing 4 to 18 carbon atoms in the ester alkyl groups. When difunctional acid monomers only are included along with the ester monomers of Formula I, the mole percent of such acid monomers should not exceed about 30 in order to maintain the required solubility parameter of between 6 and 10 $(cal/cc)^{1/2}$ in poorly hydrogen bonding solvents. A particularly preferred terpolymer is derived from 50 mole percent isooctyl acrylate, 30 mole percent stearyl methacrylate and 20 mole percent acrylic acid.

The preparation of the polymers from the monomers is well documented in the literature and can be carried out by standard bulk, solution or emulsion techniques. Generally, the latter two are preferred with solution polymerization in the oil being most preferred. The polymerization of the monomers is catalyzed by free radical-generating catalysts such as peroxides, azo catalysts and the like. To be most effective, the reactor for such polymerizations should be purged with an inert gas in order to remove traces of oxygen. The solution polymerizations are preferably run in a compatible oil solvent such that the final polymer solution preferably contains 10 to 40 percent solids.

The molecular weight of the polymers used in the compositions may vary over a broad range. The molecular weight must be suitably large to provide the requisite binding effect between the coating composition and an adhesive applied over the coating composition. The upper limit is determined largely by formulation requirements. As the molecular weight increases, the polymers tend to become too viscous to formulate easily into cosmetically appealing compositions. Generally, polymers having a Brookfield viscosity between 50 and 250,000 cps, particularly between 5,000 and 40,000 cps, when measured at about 25 percent nonvolatiles, are preferred in the practice of the present invention.

The oil carrying the acrylate polymer may be any oil or mixture of oils which is conventionally used in the cosmetic art. The oil base of the compositions may be solid or liquid, but the entire formulation should be somewhat fluid at skin temperatures for ease of application. Examples of suitable oils include saturated fatty esters and diesters such as isopropyl palmitate, isopropyl myristate, butyl stearate, diisopropyl adipate, dioctyl sebacate, propylene glycol dipelargonate, etc., paraffin oils and waxes, animal and vegetable oils including mink oil, coconut oil and derivatives thereof, palm oil, corn oil, cocoa butter, sesame oil, and the like, lanolin derivatives, fatty alcohols such as isostearyl alcohol, isocetyl alcohol, and straight chain alcohols from $C_6$–$C_{18}$, and certain petroleum distillates which are toxicologically safe such as $C_8$–$C_{18}$ isoparaffin hydrocarbon solvents. The oils mentioned in this list are merely examples and are not intended to limit the invention in any way. In general, any nonvolatile material or mixture thereof which is toxicologically safe for human use and which has a solubility parameter in the range of 6 to 10 $(cal/cc)^{1/2}$ in poorly hydrogen-bonding solvents may be used as the emollient oil in the compositions of the invention.

Emollient oils which are particularly preferred in the practice of the present invention include petrolatum, cetyl palmitate, cetyl/stearyl alcohol, propylene glycol, dicaprylate/dicaprate, 15 mole propoxylate of stearyl alcohol, silicone fluids, 2 mole propoxylate of myristyl propionate and "PPG-15 Stearyl Ether", commercially available from ICI Americas, Inc., Wilmington, Del.

Preferably, the compositions useful in the practice of the present invention are emulsions in the form of lotions or creams. The emulsions are of two basic types, i.e., oil-in-water and water-in-oil emulsions. The emulsions are made by first preparing an oil phase by mixing the oil base and acrylate polymer together and warming the mixture with slow agitation to about 95° C. (203° F.). The oil formulations generally contain about 0.25 to 40 percent by weight of the acrylate polymer, with the preferred range being from about 3.0 to 10.0 percent by weight. At levels much above 20 percent, the formulation generally becomes sticky and unpleasant feeling.

The preferred acrylate polymers for the emulsion formulations are insoluble in water and have a solubility parameter between about 6 and 10 $(cal/cc)^{1/2}$ in poorly hydrogen bonding solvents. The method for determining solubility parameter ranges of polymers and an extensive list of solvents (classified as either poorly hydrogen bonding, moderately hydrogen bonding, or strongly hydrogen bonding) are described in Polymer Handbook (edited by Bandrup and Immergut), pages IV-344-358 (1966), incorporated herein by reference. Acrylate polymers having the requisite solubility parameter will be soluble in the oil base of the compositions. It is also preferred to use acrylate polymers having emulsifying properties (i.e., those containing between 10 and 50 mole percent of acid monomers). Auxiliary emulsifiers may be employed to extend shelf life, but in general, the polymers alone are able to give emulsions with good stability. One particularly useful additive which has been employed is a copolymer of ethylene and acrylic acid (available commercially from Allied Chemical as "AC-540 Polyethylene"). This material acts as a good emulsion stabilizer, especially at higher temperatures.

The emulsions generally contain between 30 and 70 percent by weight of water. Preferably, the emulsions contain about 40 to 55 percent by weight water and 0.25 to 10 percent by weight acrylate polymer. Although water is used in the emulsions of this system, the fact that the water evaporates is not an important feature of this invention. The film that is left behind on the skin in this system is an oil film identical to the film that is coated out from the oil system. A continuous, dry, polymeric film is not cast on the skin in either case.

The emulsions are generally prepared by heating, independently, the oil phase (containing the acrylate polymer) and the water phase, and slowly adding the water phase to the oil phase with good agitation. Homogenization is preferred, but it is not necessary. Humectants are also advantageously incorporated into the water phase of the compositions of the present invention. Suitable humectants include, but are not limited to, polyols, such as glycerine, propylene glycol, dipropylene glycol, polypropylene glycol, glycerine ethoxylates, methyl glucose ethoxylates, polyethylene glycol, polyethylene/polypropylene glycols, sorbitol, and α-hydroxy acids (e.g., glycolic acid or the ammonium salt of lactic acid). Dipropylene glycol and polypropylene glycol are particularly preferred as humectants.

The addition of low levels of stabilizing ingredients in the water phase has been shown to be helpful. Salts such as magnesium sulfate have proven to be useful emulsion stabilizers, and they do not significantly affect the water resistance of the formulations. The addition of water soluble gums such as guar derivatives, xanthan gum, and aloe vera and thickeners such as hydroxy ethyl cellulose, hydroxy methyl cellulose and carboxyl vinyl polymers have been found to be helpful in stabilizing the emulsion.

The addition of the silicone oil dimethicone to the oil phase prior to preparation of the emulsion has been found to improve the ability of the emulsions to act as a barrier to urine, feces or other indigenous and exogenous materials. Preferably the dimethicone is present in concentrations up to 5 percent by weight of the emulsion. Fragrances, dyes, colorants, preservatives, antioxidants, antimicrobials and other such materials conventionally used in moisturizing compositions may also be included in minor amounts in the compositions without affecting the substantivity of the compositions. These materials are normally added after the emulsions have been prepared and cooled.

Any oil-in-water or water-in-oil emulsifying agent conventionally used in cosmetic formulations may be used in the emulsions of the present invention. It has been found, however, that the emulsifier can influence substantivity to some extent. Emulsifiers which provide good substantivity include the 82-mole ethoxylate of glyceryl tallowate, glyceryl stearate, and the 20-mole ethoxylate of cetyl/stearyl alcohol. The emulsifier is preferably present in an amount ranging from about 1 to 10 percent by weight of the composition and preferably, 2 to 4 percent by weight.

Combinations of emulsifying agents provide a means of further stabilizing the emulsions. Increased stability has been realized with a number of surfactant pairs but combinations of polyoxyethylene 2 stearyl ether and polyoxyethylene 21 stearyl ether have been particularly preferred in this regard. More specifically, cream compositions incorporating these two emulsifying agents in a range from about 1 to 15 percent by weight of the composition, and more preferably from about 4 to 6 percent by weight, wherein the surfactants are present in a ratio of from about 95:5 to 70:30, or more preferably in a ratio of 85:15, have shown significantly improved stability.

When applied to human skin, these emulsions form an oil film on the skin surface. Surprisingly, in spite of the oiliness and moisturizing effects of the emulsions, pressure sensitive adhesives, such as medical tapes, adhere at least as well and, in most cases, more strongly to treated skin than to untreated skin. Medical tapes which adhere particularly well to the emulsions include those utilizing acrylate and rubber based pressure sensitive adhesives. Examples are "3M Brand Transpore™Tape", "3M Brand Blenderm™Tape", "3M Brand Steri-Strips™" and "3M Brand Micropore™Tape".

The treatments of this invention are water-repellant, moisturizing and long lasting compared to other commercially available skin lotions. These features are important for ostomy or incontinence applications where protection of the skin from irritating body fluids such as urine, feces and intestinal fluids is desired. The fact that the treatments enhance adhesion of pressure sensitive adhesives, allows the treatments to be used to protect skin surrounding stomas, dermal ulcers, diseased skin or surgical wounds without interfering with the application of adhesive wound dressings.

The compositions useful in the practice of the invention are further illustrated by the following nonlimiting examples.

EXAMPLES

Swine Model Peel Adhesion Test

The ability of the substantive skin creams of the present invention to enhance tape adhesion to skin was measured by using a Swine Model Peel Adhesion Test which was conducted according to the following protocol. The pigs were anesthetized, their backs and flanks clipped, shaved, washed, wiped clean with alcohol, towel dried and allowed to air dry. Test formulations were applied to one side of the pig's back at a rate of approximately 0.02 gm/cm$^2$, the formulation allowed to air dry for at least 5 minutes and the 25 mm×75 mm strips of "3M Brand Micropore™Tape" were applied to both the treated and the untreated, (control side) of the pig's back. After 30 minutes, peel adhesion values were determined by removing the tape strips from the pig's back at a rate of 15 cm/sec (6 in/sec) using a calibrated mechanical peel adhesion testing device. The initial peel angle was approximately 180° but it gradually decreased to about 90° as the tape strip was peeled away from the pig's backbone. The peel adhesion testing device consisted of a calibrated load cell attached to a constant speed motor which was attached to a cord, which passed through a pulley arrangement, that was terminated at the opposite end with a clamp. The clamp was attached to the end of the tape strip nearest the pig's backbone. Peel adhesion values were an average of the indicated number of replicates and are reported in gms/2.54 cm width. The peel adhesion values were dependent to some extent upon the location of the body site, for example, the amount of hair and skin mobility at that site. Care was taken to assure that the same body site was used for the treated and control samples.

The impact on peel adhesion of several components of the cream formulation was independently studied to develop an optimum formulation that balanced peel adhesion enhancement and minimized skin stripping, especially to compromised skin. Variables which were investigated included the composition of the acrylate terpolymer, the concentration of the acrylate terpolymer in the oil phase of the formulation, and the concentration of the emollient dicapryl adipate in the formulation.

It should be noted that this test provides only an indication of adhesive performance on mammalian skin. The test focuses on short term (30 min.) adhesive values and does not take into consideration the adhesive build that occurs over extended contact time with virtually all medical adhesives. Additionally, it does not consider the many variables associated with mammalian skin (e.g., oil content) that can influence adhesive performance.

Examples 1–12

Terpolymer Preparation

Isopropyl palmitate (IPP, Emerest 2316, available from Malmstrom Chemicals, Emery Industries, Inc.), isooctyl acrylate ("IOA" available from Aldrich Chemicals, Milwaukee, Wis.), stearyl methacrylate, acrylic acid, and benzoyl peroxide (0.57 gms), were charged into one quart bottles in the ratios indicated in Table 1 and the reactants degassed by drawing a vacuum on the bottles and releasing the vacuum with nitrogen. (The IOA:SMA:AA ratios shown in Table 1 are independent of the IPP.) The bottles were capped and placed in an Atlas Launderometer (commercially available from Atlas Electrical Devices, Co., Chicago, Ill.) at 60° C. for 16 hours. After cooling, the polymer solutions (originally 30–40% solids) were diluted with additional IPP to produce 25% solids solutions. Viscosities of 25% solids solutions of the various terpolymer compositions were measured using a Brookfield viscometer with a #3 Spindle rotating at 30 rpm. The results are reported in Table 1.

TABLE 1

TERPOLYMER COMPOSITIONS

| Example No. | IPP (gms) | Molar Ratios IOA/SMA/AA | Gms (moles) Monomer | | | Viscosity 25% Solids Soln. (cps) |
|---|---|---|---|---|---|---|
| | | | IOA | SMA | AA | |
| 1 | 120 | 90:10:0 | 66.4 (0.36) | 13.6 (0.04) | 0.0 (0.0) | 1,720 |
| 2 | 120 | 60:40:0 | 36.0 (0.20) | 44.0 (0.13) | 0.0 (0.0) | 3,410 |
| 3 | 120 | 80:10:10 | 62.5 (0.34) | 14.4 (0.42) | 3.1 (0.042) | 2,490 |
| 4 | 120 | 50:40:10 | 31.4 (0.17) | 46.2 (0.136) | 2.4 (0.033) | 5,510 |
| 5 | 120 | 50:30:20 | 35.4 (0.19) | 39.0 (0.115) | 5.5 (0.076) | 8,300 |
| 6 | 140 | 50:30:20 | 26.6 (0.144) | 29.3 (0.086) | 4.1 (0.057) | 2,520 |
| 7 | 130 | 60:10:30 | 46.6 (0.253) | 14.3 (0.042) | 9.1 (0.130) | 18,500 |
| 8 | 130 | 30:40:30 | 18.2 (0.089) | 44.6 (0.132) | 7.2 (0.160) | 14,100 |
| 9 | 140 | 20:40:40 | 11.0 (0.089) | 40.4 (0.119) | 8.6 (0.119) | 13,400 |
| 10 | 140 | 25:35:40 | 14.3 (0.078) | 42.8 (0.126) | 8.9 (0.123) | 17,200 |
| 11 | 140 | 10:40:50 | 5.8 (0.031) | 42.8 (0.126) | 11.4 (0.158) | 73,300 |
| 12 | 140 | 20:30:50 | 12.7 (0.069) | 34.9 (0.103) | 12.4 (0.172) | 50,400 |

The concentrations of all three monomers (i.e., IOA, SMA and AA) in the terpolymer were varied in this study to determine which monomer or combinations of monomers influenced peel adhesion. Each of the diluted terpolymer solutions (25% solids) was applied to a pig's back in accordance with the previously described Swine Model Peel Adhesion Test Protocol to assess the impact of the compositional changes on peel adhesion. Data from the peel adhesion study for the various terpolymer compositions is reported in Table 2.

TABLE 2

SWINE MODEL PEEL ADHESION DATA

| Example No. | Mole % AA | Repli- cates | Peel Adhesion (gms/2.54 cm) Treated | Peel Adhesion (gms/2.54 cm) Control | Difference in Peel Adhesion |
|---|---|---|---|---|---|
| 1 | 0 | 10 | 17 | 22 | (5) |
| 2 | 0 | 10 | 17 | 37 | (20) |
| 3 | 10 | 9 | 46 | 30 | 16 |
| 4 | 10 | 8 | 54 | 38 | 16 |
| 5 | 20 | 10 | 108 | 27 | 81 |
| 6 | 20 | 8 | 92 | 30 | 62 |
| 7 | 30 | 10 | 192 | 49 | 143 |
| 8 | 30 | 10 | 184 | 31 | 153 |
| 9 | 40 | 8 | 157 | 32 | 125 |
| 10 | 40 | 8 | 68 | 30 | 38 |
| 11 | 50 | 8 | 68 | 35 | 33 |
| 12 | 50 | 8 | 93 | 29 | 64 |

This data illustrates that terpolymer compositions having between about 10 to about 50 mole percent AA would be functional on uncompromised mammalian skin. Generally speaking, terpolymers having less than about 10 mole percent AA demonstrated lesser peel adhesion enhancement whereas terpolymers having about 30 mole % AA demonstrated maximum peel adhesion enhancement. It should be understood, however, that satisfactory skin cream formulations could be prepared from terpolymers having AA contents above or below the optimum range by incorporating more or less of the terpolymer, respectively, in cream formulation to adjust for peel adhesion.

Examples 13–15

A comparative peel adhesion enhancement study was conducted wherein terpolymer having an AA content in the optimum range was incorporated into the oil phase and into a water-in-oil cream formulation. Peel adhesion enhancement of the oil phase was compared to the cream formulation with terpolymer and to a commercially available skin moisturizer cream ("Sween™Cream" commercially available from Sween Corp., Mankato, Minn.) which does not interfere with tape adhesion to skin.

The oil phase (Example 14) (prepared according to U.S. Pat. No. 4,172,122, incorporated herein by reference) contained the following ingredients: Terpolymer of Example 5 (9.07 parts of a 25% solids solution), light mineral oil (3.30 parts, available from Witco Chemical, New York, N.Y.), paraffin wax (1.24 parts, available from Harry Holland Distribution, Willow Brook, Ill.), ethylene/acrylic acid copolymer (2.27 parts, commercially available as "AC-540 Polyethylene" from Allied-Signal, Inc., Morristown, N.J.), coconut oil (7.83 parts, available from Universal Edible Oils, Inc., Chicago, Ill.), "PPG-15 Stearyl Ether" (7.73 parts, commercially available from ICI Americas, Inc., Wilmington, Del.), and dicapryl adipate (11.64 parts, available from Union Camp, Corp., Jacksonville, Fla.). The water phase for the cream formulation contained the following ingredients: deionized water (51.3 parts), magnesium sulfate heptahydrate (0.31 parts, available from Mallinckrodt, Chemicals, St. Louis, Mo.), and propylene glycol (4.97 parts, available from Worum Chemical Co., St. Paul, Minn.). The water-in-oil cream formulation (Example 13) was prepared by heating the oil phase to approximately 95° C. (203° F.) with slow agitation, heating the water phase, in a separate vessel, to approximately 95° C. (203° F.) with moderate agitation, adding the water phase to the oil phase with rapid agitation and cooling the resulting creamy mixture to approximately 71° C. (160° F.). Germaben II (0.75 parts), a broad spectrum antimicrobial preservative available from Sutton Laboratories, Chatham, N.J., was added to the mixture and the resulting mixture was homogenized to produce particles having a diameter of less than about 10 microns to produce a stable emulsion.

The oil phase (Example 14), the cream with terpolymer of Example 5 (Example 13), and "Sween™Cream" (Example 15) were applied to a pig's back in accordance with the previously described Swine Model Peel Adhesion Test protocol to assess peel adhesion enhancement performance. Data from this comparative study is presented in Table 3.

TABLE 3

COMPARATIVE PEEL ADHESION STUDY

| Example No. | Composition | Repli- cates | Peel Adhesion (gms/2.54 cm) Treated | Peel Adhesion (gms/2.54 cm) Control | Difference in Peel Adhesion |
|---|---|---|---|---|---|
| 13 | Cream with Terpolymer | 10 | 65 | 26 | 39 |
| 14 | Oil Phase | 10 | 62 | 21 | 41 |
| 15 | Sween ™ Cream | 10 | 22 | 20 | 2 |

The data indicates that there is a close parallel in adhesion enhancement performance between the oil phase and the cream formulation. This observation was very important in that it allowed subsequent screening evaluations of formulations in the oil phase without having to formulate the cream. "Sween™Cream" exhibited a null effect, neither increasing nor decreasing adhesion to skin.

Examples 16–26

The comparative peel adhesion enhancement study reported in Table 3 demonstrated the importance of the presence of the terpolymer in the skin cream (or oil phase) to realize significant peel adhesion enhancement. The following study examined peel adhesion enhancement as a function of the concentration of the terpolymer in the oil phase of the cream formulation. The oil phase was formulated as described in Examples 13–15, except that the terpolymer was that used in Examples 4, 5 and 9 (as indicated in Table 4) and the concentration of terpolymer was varied from 0 to 30 percent by weight of the formulation (also as indicated in Table 4) while the other components of the formulation were kept in the same relative ratios. Peel adhesion data for the various oil phase formulations using the Swine Model Peel Adhesion Test is reported in Table 4.

TABLE 4

PEEL ADHESION ENHANCEMENT STUDY OF TERPOLYMER CONCENTRATION

| Ex. No. | Ter- polymer (Example No.) | Mole % AA in Ter- poly- mer | Ter- poly- mer Conc. (wt. %)[1] | Rep- li- cates | Peel Adhesion (gms/2.54 cm) Treated | Peel Adhesion (gms/2.54 cm) Control | Diff- er- ence in Peel Ad- he- sion |
|---|---|---|---|---|---|---|---|
| 16 | 5 | 20 | 0 | 8 | 26 | 32 | (6) |
| 17 | 5 | 20 | 1 | 8 | 37 | 31 | 6 |

TABLE 4-continued

PEEL ADHESION ENHANCEMENT
STUDY OF TERPOLYMER CONCENTRATION

| Ex. No. | Ter-polymer (Example No.) | Mole % AA in Ter-poly-mer | Ter-poly-mer Conc. (wt. %)[1] | Rep-li-cates | Peel Adhesion (gms/2.54 cm) | | Diff-er-ence in Peel Ad-he-sion |
|---|---|---|---|---|---|---|---|
| | | | | | Treated | Control | |
| 18 | 5 | 20 | 3 | 10 | 37 | 26 | 11 |
| 19 | 5 | 20 | 5 | 10 | 50 | 27 | 23 |
| 20 | 5 | 20 | 9.8 | 10 | 62 | 21 | 41 |
| 21 | 5 | 20 | 20 | 10 | 63 | 30 | 33 |
| 22 | 5 | 20 | 30 | 10 | 78 | 28 | 50 |
| 23 | 4 | 10 | 20 | 7 | 27 | 34 | (7) |
| 24 | 4 | 10 | 30 | 7 | 16 | 32 | (16) |
| 25 | 9 | 40 | 1 | 7 | 32 | 34 | (2) |
| 26 | 9 | 40 | 0.5 | 9 | 18 | 28 | (10) |

[1]based upon a terpolymer concentration calculated for a water-in-oil emulsion made in accordance with Example 13.

The data in Table 4 indicates that for the terpolymer of Example 5 (containing 20 mole % acrylic acid) the optimum concentration of terpolymer in the oil phase is approximately 10 wt. percent of a 25 percent solids solution, and useful concentrations are 1 to 30 wt. percent of a 25 percent solids solution. This study also suggests that terpolymers having an acrylic acid (AA) content significantly different than 20 mole % AA are less preferred components for the cream formulations of the invention, even if the oil phase composition is adjusted to bring the AA content of the formulation into the preferred range.

Example 27

A water-in-oil cream formulation was prepared using the following oil and water phase compositions and the formulation procedure described in Example 13.

An oil phase consisting of the terpolymer of Example 5 (9.8 parts of an approximately 25% solids solution in IPP), light mineral oil (3.5 parts), paraffin wax (1.3 parts), ethylene/acrylic acid copolymer (2.5 parts), coconut oil (8.5 parts), PPG-15 stearyl ether (8.4 parts), and dicapryl adipate (12.6 parts).

A water phase consisting of deionized water (42.6 parts), magnesium sulfate heptahydrate (0.3 parts), and dipropylene glycol (9.4 parts).

The water-in-oil emulsion was prepared by combining the oil and water phases as described in Example 13. Germaben II (0.8 parts) was added and the resulting mixture was homogenized to produce particles having a diameter of less than 10 microns. A fragrance, Gentle Floral No. A 10390 from Haarmann Reimer Corp., Springfield, N.J. (0.25 parts), was added to the homogenized mixture after it had cooled to approximately 40° C.

Example 28

Water-in-oil cream formulations of the present invention having improved stability can be prepared by utilizing combinations of surfactants. Thus, a water-in-oil cream formulation was prepared using the following oil and water phase compositions and the formulation procedure described in Example 27.

The oil phase consisting of the terpolymer of Example 5 (8.7 parts of an approximately 25% solids solution in IPP), light mineral oil (3.1 parts), paraffin wax (1.2 parts), ethylene/acrylic acid copolymer (2.2 parts), coconut oil (7.5 parts), PPG-15 stearyl ether (9.45 parts), polyoxyethylene 21 stearyl ether (0.6 parts), available from ICI Americas, Inc., polyoxyethylene 2 stearyl ether (3.4 parts), available from ICI Americas, Inc., and dicapryl adipate (12.6 parts).

A water phase consisting of deionized water (43 parts), magnesium sulfate heptahydrate ((0.3 parts), and dipropylene glycol (8.3 parts).

Examples 29–32

Substantive/adhesion enhancing skin cream formulations can also be prepared as oil-in-water emulsions with slight modifications to the overall formulation. Table 5 reports results of the Swine Model Peel Adhesion Test for a range of oil phase compositions based on the terpolymer of Example 5 as well as a complete oil-in-water emulsion composition. The oil and water phases were prepared as described in Examples 13–15. The compositions of Examples 29–32 are in the oil phase. The oil-in-water emulsion (Example 32) was prepared according to the procedure of Example 13.

TABLE 5

OIL-IN-WATER EMULSION STUDIES

| | Example No. | | | |
|---|---|---|---|---|
| Components | 29 (Oil) | 30 (Oil) | 31 (Oil) | 32 (Emulsion) |
| Terpolymer (gms) | 0.25 | 5.0 | 2.5 | 2.5 |
| % Terpolymer (by wt.)[1] | 1.0 | 20 | 9.8 | 9.8 |
| Mineral Oil (gms) | 3.3 | 2.67 | 3 | 3 |
| Coconut Oil (gms) | 1.43 | 1.16 | 1.3 | 1.3 |
| Pomulgen G[2] (gms) | 2.2 | 1.78 | 2.0 | 2.0 |
| Adol 63[3] (gms) | 1.65 | 1.33 | 1.5 | 1.5 |
| Aloe Vera Gel[4] (gms) | — | — | — | 0.5 |
| Glydent[5] (gms) | — | — | — | 0.3 |
| Keltrol[6] (gms) | — | — | — | 0.5 |
| D.I. water (gms) | — | — | — | 79.4 |
| Germaben II (gms) | — | — | — | 0.8 |

[1]based upon a terpolymer concentration calculated for a water-in-oil emulsion made in accordance with Example 13
[2]an emulsifying agent available from Americol Corp., Edison, NJ
[3]an emulsifying agent available from Sherex Co., Dublin, OH
[4]available from Costec Corp., Palatine, IL
[5]a preservative available from Lonza Corp., Far Lawn, NJ
[6]xanthan gum available Merk Co., Chicago, IL All four compositions (Examples 29–32) were evaluated in a Swine Model Peel Adhesion Test, as previously described, to determine the level of adhesion enhancement, the results of which are reported in Table 6.

TABLE 6

PEEL ADHESION ENHANCEMENT STUDY
OF OIL-IN-WATER EMULSION

| Example No. | Terpoly-mer Conc. (% by wt.)[1] | Repli-cates | Peel Adhesion (gms/2.54 cm) | | Difference in Peel Adhesion |
|---|---|---|---|---|---|
| | | | Treated | Control | |
| 29 (Oil) | 1.0 | 7 | 40 | 26 | 14 |
| 30 (Oil) | 20 | 7 | 78 | 28 | 50 |
| 31 (Oil) | 9.8 | 7 | 53 | 34 | 19 |

TABLE 6-continued

PEEL ADHESION ENHANCEMENT STUDY
OF OIL-IN-WATER EMULSION

| Example No. | Terpolymer Conc. (% by wt.)[1] | Replicates | Peel Adhesion (gms/2.54 cm) Treated | Peel Adhesion (gms/2.54 cm) Control | Difference in Peel Adhesion |
|---|---|---|---|---|---|
| 32 (Emulsion) | 9.8 | 9 | 41 | 34 | 7 |

[1]based upon a terpolymer concentration calculated for a water-in-oil emulsion made in accordance with Example 13.

The correlation between adhesion enhancement of the oil phase and the emulsion is not as pronounced with the oil-in-water emulsion as it is with the water-in-oil emulsions. There is never-the-less an indication that tape adhesion will be as good as or better than it would be without the skin cream.

What is claimed is:

1. A method of moisturizing mammalian skin without adversely affecting the adhesion of a acrylate or rubber based pressure sensitive adhesive comprising the steps of
    (1) coating the skin with a composition comprising
        (a) an effective amount of an acrylate polymer which has a solubility parameter of between about 6 and 10 $(cal/cc)^{1/2}$ in poorly hydrogen bonding solvents, said polymer comprising:
            (i) from 40 to 95 mole percent of the same or different ester monomers of the formula:

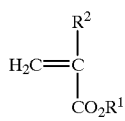

wherein
$R^1$ is an alkyl radical containing 4 to 18 carbon atoms in cyclic, straight- or branched-chain configuration, and
$R^2$ is hydrogen or lower alkyl containing 1 to 4 carbon atoms; and
            (ii) from 5 to 60 mole percent by weight of the same or different acid monomers of the formula:

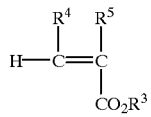

wherein
$R^3$ is H or an alkyl group containing 1 to 18 carbon atoms;
$R^4$ is hydrogen, methyl, or $-CO_2R^3$, and
$R^5$ is hydrogen, lower alkyl or $-CH_2CO_2R^3$; provided when $R^4$ is not hydrogen, $R^5$ is hydrogen and when $R^5$ is not hydrogen, $R^4$ is hydrogen, and further provided that at least one $R^3$ is hydrogen;
        (b) dissolved in a nonvolatile emollient oil conventionally used in the cosmetic art, which emollient oil has a solubility parameter in the range of 6 to 10 $(cal/cc)^{1/2}$ in poorly hydrogen-bonding solvents; which composition dries to a coating comprising at least 60 percent by weight of said emollient oil; and
    (2) applying said pressure sensitive adhesive over said composition;
wherein said acrylate polymer is formulated such that the adhesion of said pressure sensitive adhesive to said composition is greater than the adhesion of said pressure sensitive adhesive to skin coated with emollient oil alone.

2. The method according to claim 1 wherein said acrylate polymer comprises 15 to 30 mole percent of said acid monomers.

3. The method according to claim 2 wherein said acrylate polymer comprises 70 to 85 mole percent of said ester monomers.

4. The method according to claim 1 wherein said ester monomers are selected from the group consisting of acrylates and methacrylates with alkyl groups containing 6 to 18 carbon atoms.

5. The method according to claim 1 wherein said acid monomers and selected from the group consisting of acrylic acid, methacrylic acid, maleic acid, itaconic acid and ethacrylic acid.

6. The method according to claim 1 wherein said oil is a saturated fatty ester or diester.

7. The method according to claim 1 wherein said acrylate polymer is present in a concentration of about 10 to 40 percent by weight of said oil.

8. The method according to claim 1 wherein the amount of additional emollient oil present in said composition is sufficient to bring the concentration of said acrylate polymer to between about 0.5 to 20.0 percent by weight of said composition.

9. The method of claim 1 wherein said polymer is a terpolymer of isooctyl acrylate, stearyl methacrylate acrylic acid.

10. The method of claim 9 wherein said terpolymer comprises about 50 mole percent isooctyl acrylate, about 30 mole percent stearyl methacrylate and about 20 mole percent acrylic acid.

11. The method according to claim 1 wherein said oil comprises one or more oils selected from the group consisting of saturated fatty esters and diesters, paraffin oils and-waxes, animal and vegetable oils, lanolin derivatives, fatty alcohols, and non-toxic petroleum distillates.

12. The method according to claim 1 wherein said coating composition is an emulsion of said oil and a water phase.

13. The method of claim 12 wherein said acrylate polymer is present in said emulsion in a concentration of about 0.25 to 10.0 percent by weight of said emulsion.

14. The method of claim 12 wherein said emulsion is a water-in-oil emulsion wherein said water phase is present in a concentration of about 30 to 70 percent by weight of said emulsion.

15. The method of claim 12 wherein said emulsion is an oil-in-water emulsion wherein said water phase is present in a concentration of about 30 to 70 percent by weight of said emulsion.

16. A composite structure applied to mammalian skin comprising
    (a) a coating applied to said skin, said coating comprising at least 60 percent by weight of a nonvolatile emollient oil base conventionally used in the cosmetic art, which emollient oil has a solubility parameter in the range of 6 to 10 $(cal/cc)^{1/2}$ in poorly hydrogen-bonding solvents, and an effective amount of an acrylate polymer dissolved therein, said acrylate polymer having a solubility parameter of about 6 to 10 $(cal/cc)^{1/2}$ in poorly hydrogen-bonding solvents and said acrylate polymer comprising:

from about 40 to 95 mole percent of the same or different ester monomers of the formula:

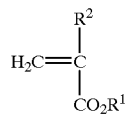

wherein
$R^1$ is an alkyl radical containing 4 to 18 carbon atoms in cyclic, straight- or branched-chain configuration, and
$R^2$ is hydrogen or lower alkyl containing 1 to 4 carbon atoms; and
from about 5 to 60 mole percent by weight of the same or different acid monomers of the formula:

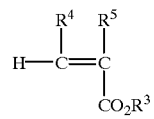

wherein
$R^3$ is H or an alkyl group containing 1 to 18 carbon atoms;
$R^4$ is hydrogen, methyl, or —$CO_2R^3$;
$R^5$ is hydrogen, lower alkyl or —$CH_2CO_2R^3$; provided when $R^4$ is not hydrogen, $R^5$ is hydrogen and when $R^5$ is not hydrogen, $R^4$ is hydrogen, and further provided that at least one $R^3$ is hydrogen; and (b) an acrylate or rubber based pressure-sensitive adhesive tape applied over said coating;

wherein said acrylate polymer is formulated such that the adhesion of said pressure sensitive adhesive to said coating is greater than the adhesive of said pressure sensitive adhesive skin coated with an emollient oil alone.

17. The composite structure of claim 13 wherein said pressure-sensitive adhesive is an acrylate.

* * * * *

UNITED STATES PATENT AND TRADEMARK OFFICE
CERTIFICATE OF CORRECTION

PATENT NO. : 6,200,596 B1　　　　　　　　　　　　　　　　　　　　　Page 1 of 1
DATED : March 13, 2001
INVENTOR(S) : Donald A. Schwartzmiller and Neil A. Randen It is certified that error appears in the above-identified patent and that said Letters Patent is hereby corrected as shown below:

Column 1,
Line 50, "composition" should read -- compositions --.

Column 14,
Line 18, "and" should read -- are --.
Line 41, after "and" delete "-".

Signed and Sealed this

Fourth Day of December, 2001

Attest:

NICHOLAS P. GODICI
*Attesting Officer*　　　*Acting Director of the United States Patent and Trademark Office*